(12) United States Patent
Panza-Giosa et al.

(10) Patent No.: US 10,060,840 B2
(45) Date of Patent: Aug. 28, 2018

(54) METHODS OF DETERMINING STRAIN LIMITS AND DESIGNING DEVICES BASED ON STRAIN LIMITS

(71) Applicant: GOODRICH CORPORATION, Charlotte, NC (US)

(72) Inventors: Roque Panza-Giosa, Oakville (CA); Edward Benedict Evans, Toronto (CA); Hiten Awasthi, Burlington (CA)

(73) Assignee: Goodrich Corporation, Charlotte, NC (US)

( * ) Notice: Subject to any disclaimer, the term of this patent is extended or adjusted under 35 U.S.C. 154(b) by 275 days.

(21) Appl. No.: 14/805,109

(22) Filed: Jul. 21, 2015

(65) Prior Publication Data

US 2017/0023454 A1 Jan. 26, 2017

(51) Int. Cl.
  *G01N 3/00* (2006.01)
  *G01N 3/20* (2006.01)
  *G01N 3/06* (2006.01)

(52) U.S. Cl.
  CPC ............. *G01N 3/20* (2013.01); *G01N 3/068* (2013.01); *G01N 2203/0023* (2013.01); *G01N 2203/0064* (2013.01); *G01N 2203/0647* (2013.01)

(58) Field of Classification Search
  None
  See application file for complete search history.

(56) References Cited

U.S. PATENT DOCUMENTS

| | | | | |
|---|---|---|---|---|
| 5,054,324 A | * | 10/1991 | Pohl | G01N 3/04 73/859 |
| 5,507,189 A | * | 4/1996 | Kim | G01N 3/28 73/834 |
| 8,177,953 B2 | * | 5/2012 | Nardi | G01N 3/04 202/258 |
| 8,202,627 B2 | | 6/2012 | Reath et al. | |
| 8,402,811 B2 | | 3/2013 | Nie | |
| 8,544,338 B2 | | 10/2013 | Pettit | |
| 9,784,655 B2 | * | 10/2017 | Heiss-Chouquet | G01N 3/08 |
| 2016/0033379 A1 | * | 2/2016 | Heiss-Chouquet | G01N 3/08 73/834 |

FOREIGN PATENT DOCUMENTS

| | | |
|---|---|---|
| GB | 1466875 A | 3/1977 |
| JP | H1183349 | 7/1999 |
| JP | H11183349 A * | 7/1999 |
| JP | 2000131206 | 5/2000 |
| JP | 2000131206 A * | 5/2000 |
| JP | 2001056275 | 2/2001 |
| WO | 2009112071 A1 | 9/2009 |

OTHER PUBLICATIONS

Extended European Search Report dated Dec. 15, 2016 in European Application No. 16180593.2.

* cited by examiner

*Primary Examiner* — Manish S Shah
*Assistant Examiner* — Jermaine Jenkins
(74) *Attorney, Agent, or Firm* — Snell & Wilmer L.L.P.

(57) ABSTRACT

A method and system is disclosed for determining upper strain limits for materials, and designing devices or components based on determined strain limits.

18 Claims, 6 Drawing Sheets

METHODS OF DETERMINING STRAIN LIMITS AND DESIGNING DEVICES BASED ON STRAIN LIMITS

BACKGROUND

Coatings such as those applied by High Velocity Oxygen-Fuel (HVOF) techniques tend to crack under mechanical load, which limits their usefulness for components typically operated under conditions of stress and strain. Cracking, for example in devices such as pistons, degrades the piston's ability to seal, for example, and retain hydraulic fluid. Additionally, certain substrates may corrode when the coating is cracked.

SUMMARY

According to various embodiments, a method is disclosed for determining upper strain limit for coatings and coated material. According to various embodiments, a test system for a 4-point bend test for determining strain limits, and the effects of strain, for coated materials, is disclosed. According to various embodiments, a method is disclosed for designing devices or components based on determining the strain limits of coated materials.

BRIEF DESCRIPTION OF THE DRAWINGS

The drawings described herein are for illustration purposes only and are not intended to limit the scope of the present disclosure in any way. The present disclosure will become more fully understood from the detailed description and the accompanying drawings wherein.

DETAILED DESCRIPTION

All ranges and ratio limits disclosed herein may be combined. It is to be understood that unless specifically stated otherwise, references to "a," "an," and/or "the" may include one or more than one and that reference to an item in the singular may also include the item in the plural.

The detailed description of exemplary embodiments herein makes reference to the accompanying drawings, which show exemplary embodiments by way of illustration and its best mode, and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Moreover, many of the functions or steps may be outsourced to or performed by one or more third parties. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

According to various embodiments, disclosed is a test method for determining the effects of strain on a material, preferably a coating material and/or a coated substrate, and in particular for determining strain limits before cracking (which may also be referred to herein as "bending limits," "upper strain limit," and/or "max strain") of a material. According to various embodiments, the test method comprises a system for a 4-point bend test. According to various embodiments, the test method comprises observing a specimen for cracking while it is under a mechanical load.

According to various embodiments, disclosed is a method for designing devices including components based on determining the strain limits of materials before cracking. According to various embodiments, the determined strain limit(s) of the material is used to optimize the design of the component(s) and/or provide optimal ("advantageous") material(s) to produce devices which will not crack under known operational conditions. Certain embodiments may also comprise adjusting operational conditions to avoid cracking of the material(s).

According to various embodiments, the materials may comprise coated or partially coated materials, and the method may apply to determining the strain limit for the coating itself, and/or the substrate/coating combination. According to various embodiments, the coatings may comprise, for example, thermal spray coatings, such as plasma sprayed coating and HVOF applied coatings, for example tungsten carbide, for example coatings comprising WC—Co, WC—Co—Cr, Ni—Cr—Mo—Fe—Co and/or $W_2C$, etc. For example, HASTELLOY C®, (comprising Ni—Cr—Mo—Fe—Co—Mn—V and Si) may be used according to certain embodiments. The coatings may be single or multi-layered coatings, according to various embodiments.

According to various embodiments, such coatings are applied over titanium alloy substrates, for example alpha titanium alloys, alpha-beta, and beta titanium alloys. Substrates may also include steel, aluminum, and/or other metals, as well as suitable non-metals and composites.

According to certain embodiments, the coated material or coating may be defined not just by inherent properties, but also by its variable properties which can be affected by, for example parameters relating to its method of formation, application, and other factors affecting its condition. Thus, the present method also relates to determining strain limits based on the variable properties of the material.

The above method can be used to design a variety of devices which are typically subject to strain and forces such as stress and/or bending during operation. Such devices may include, for example, components such as pistons, cylinder piston housings, and pins, such as used in the aerospace or automotive industries and the like, or any other coated devices and/or components that bear coatings that are susceptible to cracking under their various operating conditions.

Figure 1:
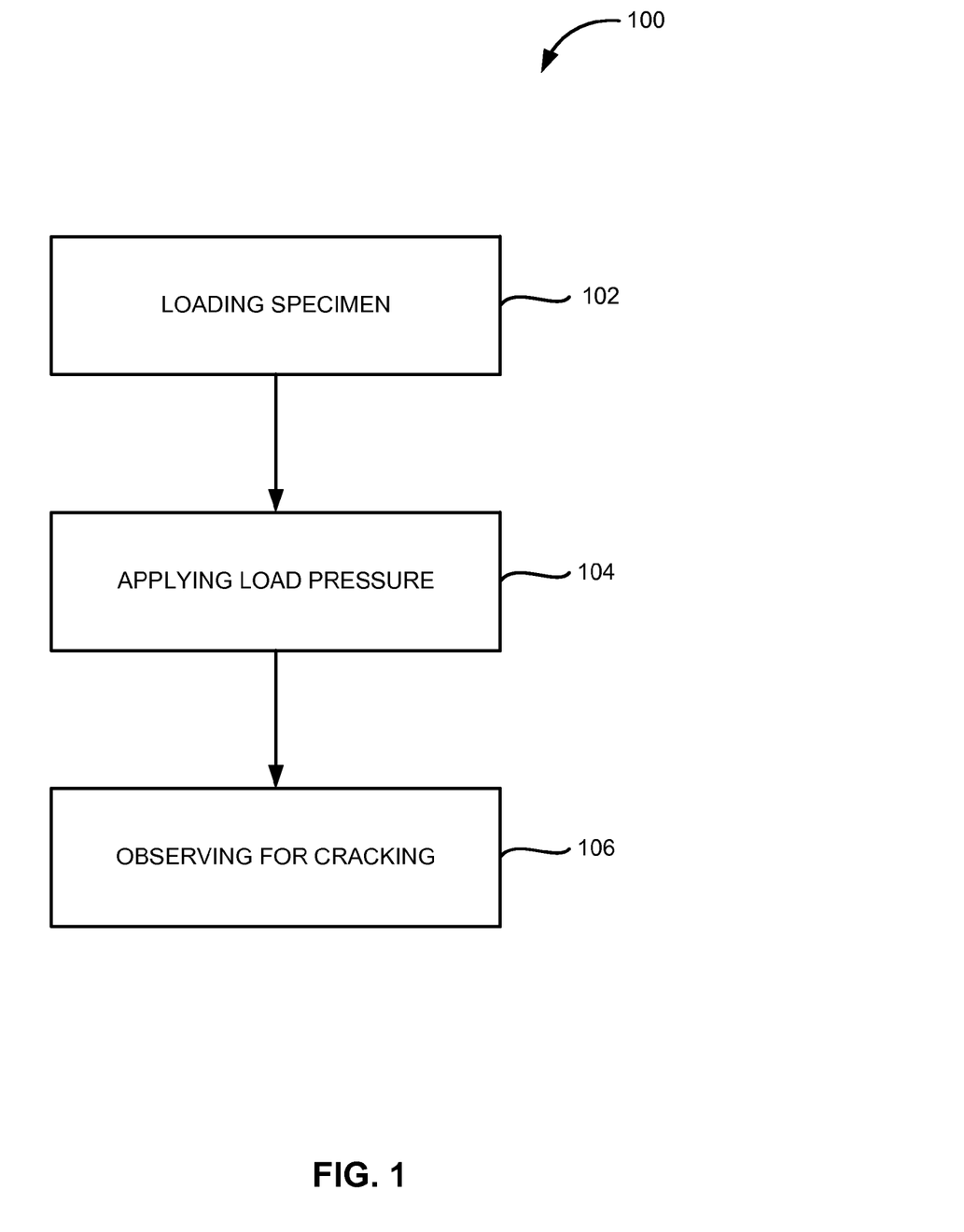
FIG. 1 illustrates a test method for determining strain limits, according to various embodiments.

A test method 100 for determining strain limits, according to various embodiments, is illustrated in FIG. 1. The method comprises loading a specimen 102 in a load fixture comprising contacting members ("load contact members") for contacting the specimen at contact sections ("contact points") on the specimen; applying load pressure 104 to the specimen at the contact points; and observing for cracking 106, wherein the specimen is observed or otherwise studied to determine whether cracking has occurred. According to various embodiments, applying load pressure 104 comprises a 4-point bend test, wherein the load fixture contacts the specimen at 4 contact points and the deforming load is a bending load. According to various embodiments, applying load pressure 104 comprises applying gradually increasing pressure (e.g. 500 lbs/s(~226 kg/s)), which may be continuous or intermittent. According to various embodiments, observing for cracking 106 comprises observing the specimen while the specimen is under the load. Additionally, observing for cracking 106 may comprise observing the specimen under magnification and/or lighting in order to detect fine micro cracks in the coating. According to various embodiments, these microcracks may be visible with the naked eye or under magnification (e.g. ×10). According to various embodiments, the onset of cracking on coatings can also be detected using a very accurate high speed camera system connected with load applying apparatus. According to various embodiments, a test system for determining strain limits comprises a test specimen, a load positioner, and a load applying apparatus. During testing, the test specimen is retained within the load positioner, and the load positioner contacts the specimen at the points where a load will be applied. The test specimen retained within the load positioner is subject to tension on the coated side via a tension applying apparatus. According to various embodiments, the load positioner and tension applicator provide an open view for allowing the specimen to be viewed during application of the load. According to various embodiments, the load positioner is set up to contact the specimen at four symmetrically distributed points along the specimen, in order to apply an evenly distributed bending force ("4-point bend test"). Other system equipment may include a deflection gauge to measure deflection of the specimen while under the load, according to various embodiments.

Figure 2A:
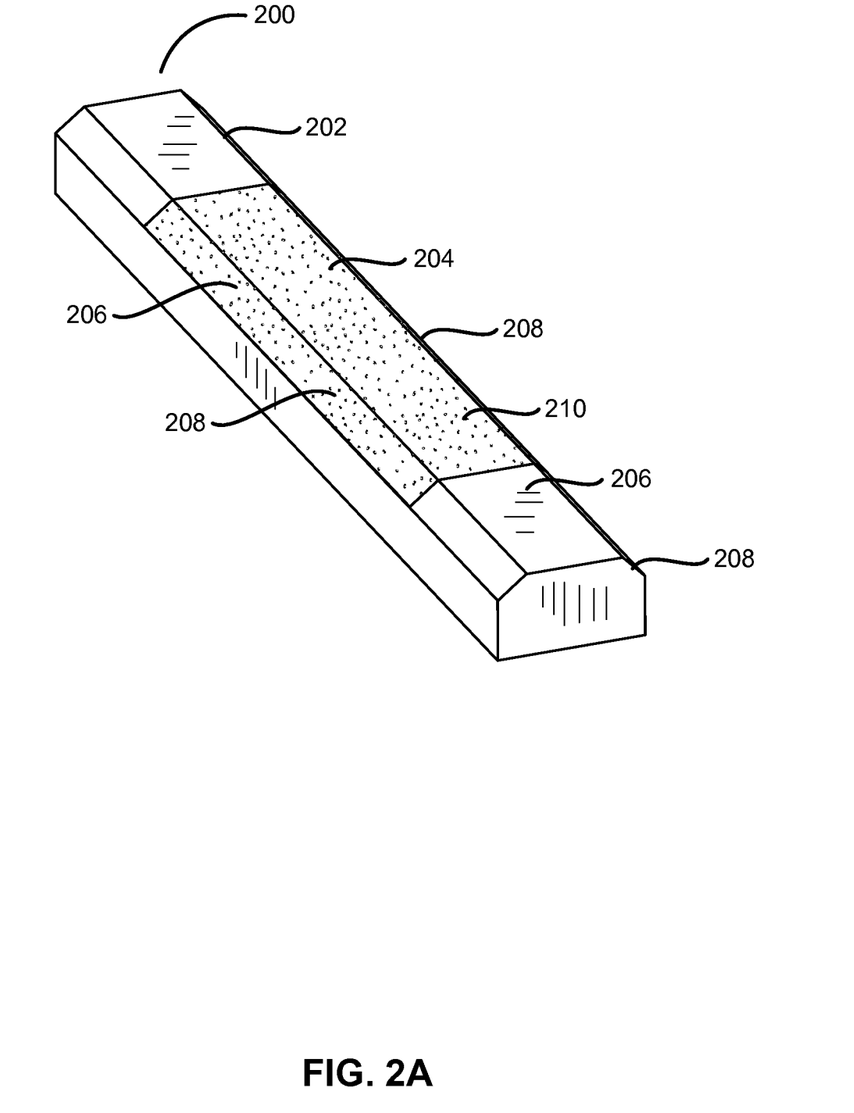
FIG. 2A is a perspective view of a specimen used in a method for determining strain limits, according to various embodiments.
Figure 2B:
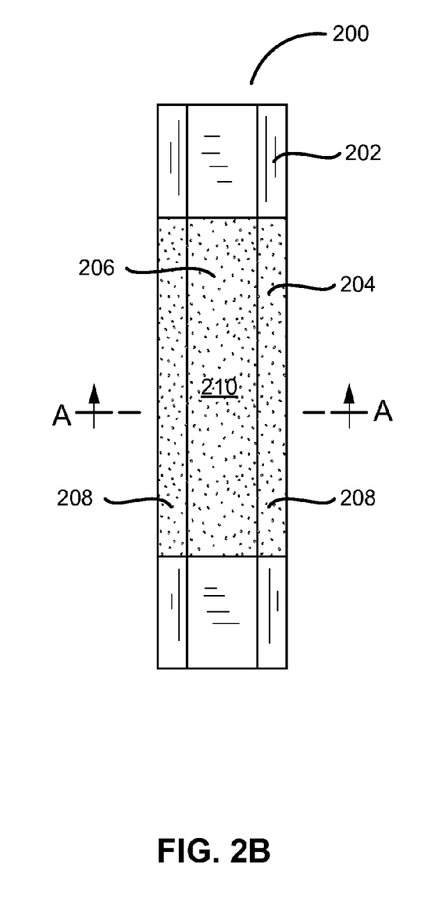
FIG. 2B is a top view of the specimen of FIG. 2A, according to various embodiments.
Figure 2C:
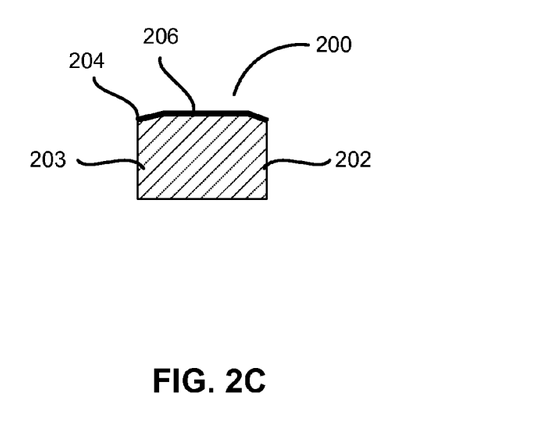
FIG. 2C is a sectional view of the specimen, through section A-A of FIG. 2B.

A test system 201 comprising a 4-point bend test, according to various embodiments, is shown in FIGS. 2A, 2B, 2C, 3, and 4. The test system 201 includes a test specimen 200, a load positioner preferably comprising a fixture 300, and a load applying apparatus, preferably comprising a tensile test machine 400. FIGS. 2A-C show test specimen 200 for test system 201, in accordance with various embodiments. Test specimen 200 comprises a substrate 202, and at least one coating layer applied to at least a portion 204 of the surface of test specimen 200 ("coated portion 204"). According to various embodiments, test specimen 200 is an elongated bar having a generally rectangular cross section 203, with beveled top edges 208, as shown in the figures. According to various embodiments, coated portion 204 covers a longitudinally centered portion of top surface 206 of substrate 202, as shown in the figures.

According to an exemplary embodiment, test specimen 200 is an HVOF coated steel or titanium substrate (e.g. Ti-5553-1) having a width of 1.8 inches (4.572 cm), length of 7.9 inches (20.066 cm), and height of 0.787 inches (1.999 cm). Top edges 208 are beveled to provide a 1-inch (2.5 cm) wide raised flat portion 210 of top surface 206 ("raised top surface 210") with top edges 208 creating a 12-degree slope from either side. Top edges 208 and adjacent raised top surface 210 are coated along a 4.75 inch (12.065 cm) section of the length, which is longitudinally centered forming coated portion 204, as shown in the figures.

According to various embodiments, prior to coating, the substrate (or portion which is to be coated) is polished to a mirror finish. According to various embodiments including test procedures involving multiple specimens, each specimen may be lightly blasted in order to reduce surface variability and improve adhesion, for example, by propelling a grit material (e.g., aluminum oxide 100 grit), at a pressure of between about 20 psi (pounds per square inch) to about 40 psi where the term about in this context means +/−2 psi.

Figure 3:
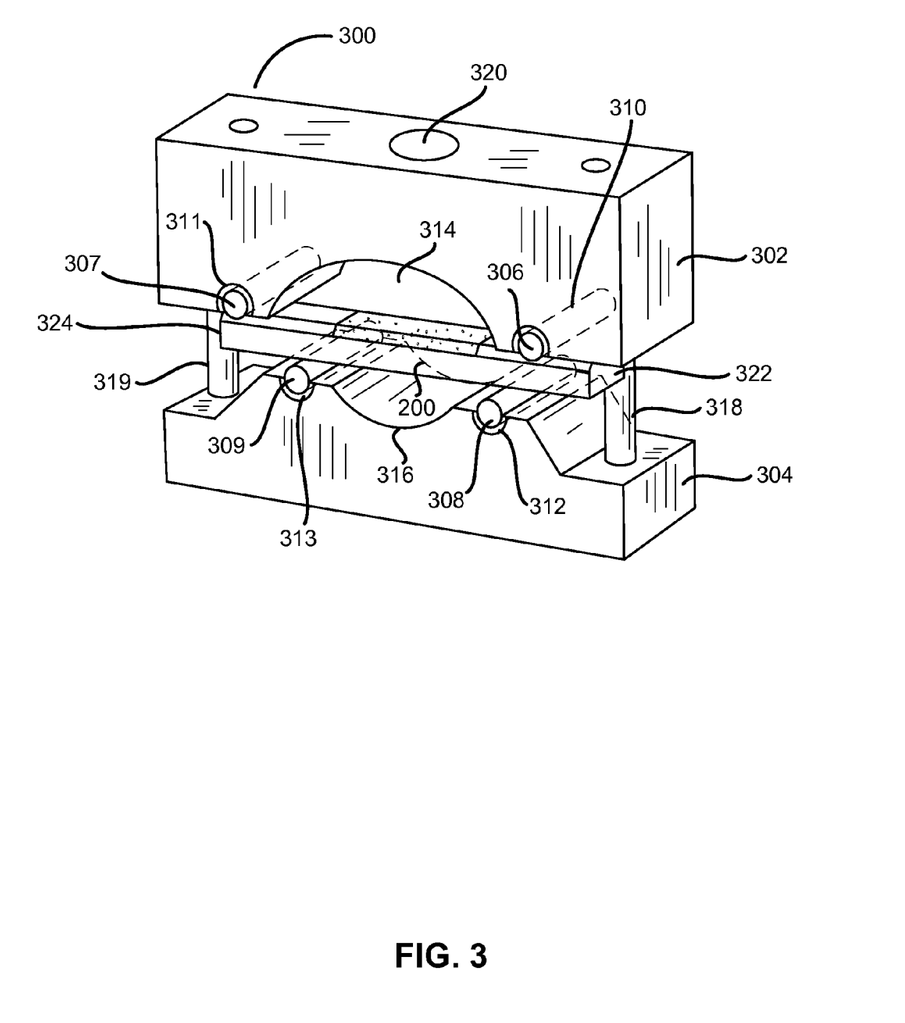
FIG. 3 is a perspective view illustrating a test set up comprising a loading fixture for a 4-point bend test, according to various embodiments.

A load positioner comprising fixture 300, into which the specimen is placed, is shown in FIG. 3, in accordance with various embodiments. Fixture 300 comprises top block 302 and bottom block 304. Blocks 302, 304 comprise a top set of contact saddles, first top saddle 306 and second top saddle 307, and a bottom set of contact saddles, first bottom saddle 308 and second bottom saddle 309, situated within top and bottom block receptacles, first top receptacle 310, second top receptacle 311, first bottom receptacle 312, and second bottom receptacle 313, for contacting test specimen 200 at four contact points, as shown in the figure. Blocks 302, 304, further comprise top and bottom arched spacings 314 and 316, respectively, and front and back fixture retainers 318 and 319 ("retainer guides") according to certain embodiments. Top block 302 further includes an observation/viewing hole 320, according to various embodiments. In the test set up, test specimen 200 is loaded and retained between the top and bottom blocks, and between retainers 318, 319, as shown in the figure. According to various embodiments, top saddles 306, 307, contact the specimen at centrally equidistant points. Likewise, bottom saddles 308, 309 contact the specimen at centrally equidistant points, wherein the distance between top saddles 306, 307 is different than the distance between bottom saddles 308, 309, as shown in the figure. This creates an evenly distributed bending strain along the coated specimen surface, resulting from a force from top saddles 306, 307, and a force from bottom saddles 308, 309, along the length of the fixture in response to a mechanical load being applied. According to various embodiments, the distance between the top saddles is greater than the distance between the bottom saddles to create a downward bend when a mechanical load is applied at the contact points. According to various embodiments, the distance between the top saddles is smaller than the distance between the bottom saddles to create an upward bend when a mechanical load is applied at the contact points.

Based on the above described 1.8 inch (4.572 cm) specimen, an exemplary set up may comprise first top saddle 306 positioned so as to contact the top of test specimen 200 0.6 inches (1.5 cm) from the front end 322, and second top saddle 307 to contact the top of test specimen 200 0.6 inches (1.5 cm) form the back end 324; and bottom saddles 308, 309, positioned so as to contact the bottom of test specimen 200 2.0 inches (5.1 cm) from the front and back ends, respectively; each saddle being a cylindrical rod having a diameter of 0.3 inches (0.76 cm). Thus, according to various embodiments, there is no contact between the coated portion and saddles, as the top saddles contact the uncoated portion of top surface 206. For this example, viewing hole 320 is approximately 2 inches in (5.1 cm) diameter to provide an adequate viewing area for the coated section of the 1.8 inch (4.6 cm) specimen. Additionally, for the specific embodiment described, the bottom arched spacing 316 has a radius of approximately 1.3 inches (3.3 cm), and the top arched spacing 314 has a radius of approximately 2.3 inches (5.84 cm). Additionally, each of retainers 318 and 319 preferably comprise a dowel pin of an approximate 0.6 inch (1.52 cm) diameter, and an approximate 5 inches (12.7 cm) length, and is situated approximately 0.73 inches (1.85 cm) from the ends of the top bock 302 and bottom block 304. In this example, the top block 302 and bottom block 304 are both approximately 10 inches (25.4 cm) in length. Top block 302 is approximately 3 inches (7.62 cm) high with first top saddle 306 and second top saddle 307 at approximately 1.65 inches (4.2 cm) from the side ends of the top block 302, and the ends of the top arched spacing 314 located approximately 2.45 inches (6.22 cm) from the side ends of the top block 302. Bottom block 304 is approximately 2.5 inches (6.35 cm) high, with a trapezoidal top portion having approximate 45 degree angled sides, at approximately 1.5 inches (3.81 cm) form the bottom of bottom block 304, as shown in FIG. 3. Additionally, first bottom saddle 308 and second bottom saddle 309 are at approximately 3.08 inches (7.8 cm) from the side ends of bottom block 304. According this example, the top block and bottom block are positioned to create a downwards bend in the specimen. According to alternate embodiments, the position of the blocks may be reversed to create an upwards bend.

Figure 4:
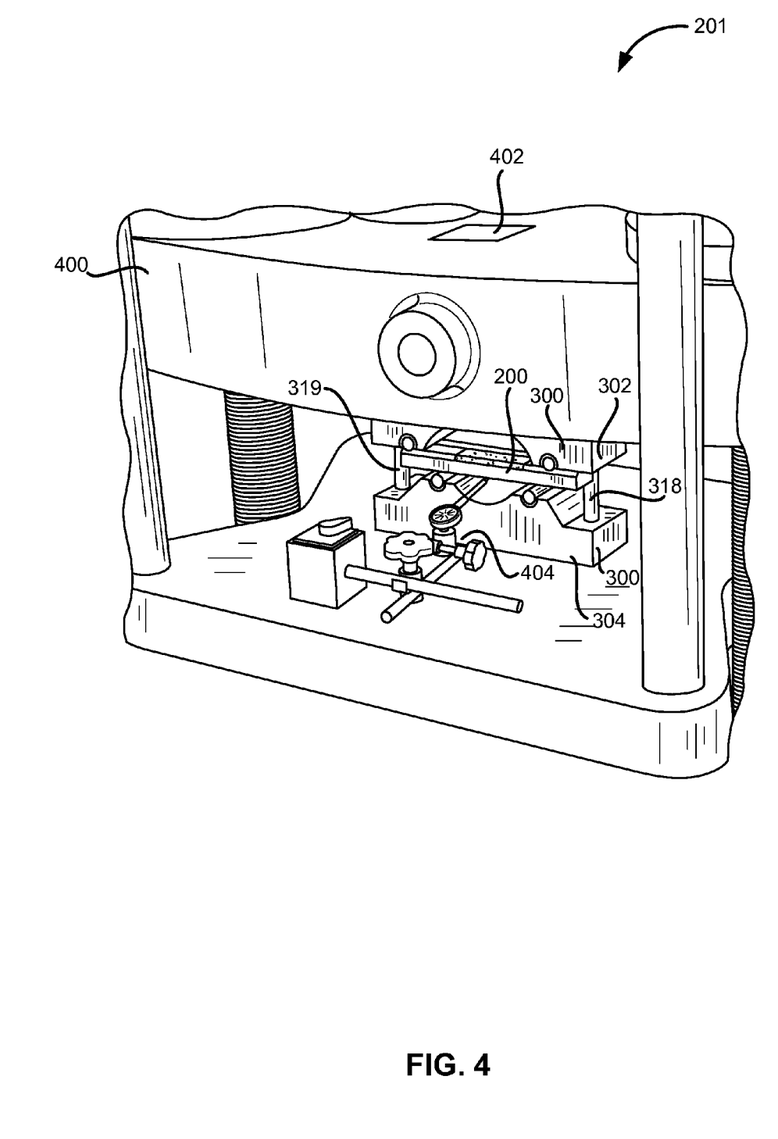
FIG. 4 is a perspective view illustrating a test set up, further comprising a tensile test machine, according to various embodiments.

As shown in FIG. 4, according to various embodiments, test specimen 200, fixture 300, are placed under a load applying apparatus comprising a tensile test machine 400, for example a programmable Tinius Olsen® machine. The machine 400 comprises an observation window 402, aligned with viewing hole 320 through which test specimen 200 may be observed. According to various embodiments, test specimen 200 is observed through viewing hole 320, through observation window 402, under magnification. Magnification may be approximately between 10× to 50×, and more preferably around 25×. Additionally, according to various embodiments, test specimen 200 is observed through viewing hole 320, through observation window 402 under illumination. This observation technique allows for accurate crack detection, as fine cracks can be seen which would otherwise close if the load on the specimen were to be removed. According to various embodiments, the onset of cracking on coatings may also be observed or detected using a very accurate high speed camera system connected with the load applying apparatus. The camera may be inserted in the viewing hole to directly observe the coating under loading. According to various embodiments, the camera control system may be programmed to stop the test when onset of cracking is observed. This may provide very accurate load measurements for the onset of cracking in various applied coatings for further optimization, and may according to various embodiments, allow for faster testing by enabling continuous pressure to be applied (as human observation, according to various embodiments, may necessitate step loading). According to various embodiments, the mechanical load is gradually increased continuously and/or incrementally, until cracking in the coating is detected. For example, the machine may be programmed to apply a load in discrete rising steps at a controlled rate (e.g. at +5000 lbf per minute or 38 kg/s), or the load may be manually increased after each observation. Additionally, a deflection gauge 404 may be set up to measure deflection of the specimen, particularly when a crack is detected. Then load is applied until cracking (of the outer fibers on the top of the polished part) is seen. Detection of cracking indicates the strain limit (which may be calculated based on the load) or point at which the coating fails.

Figure 5:
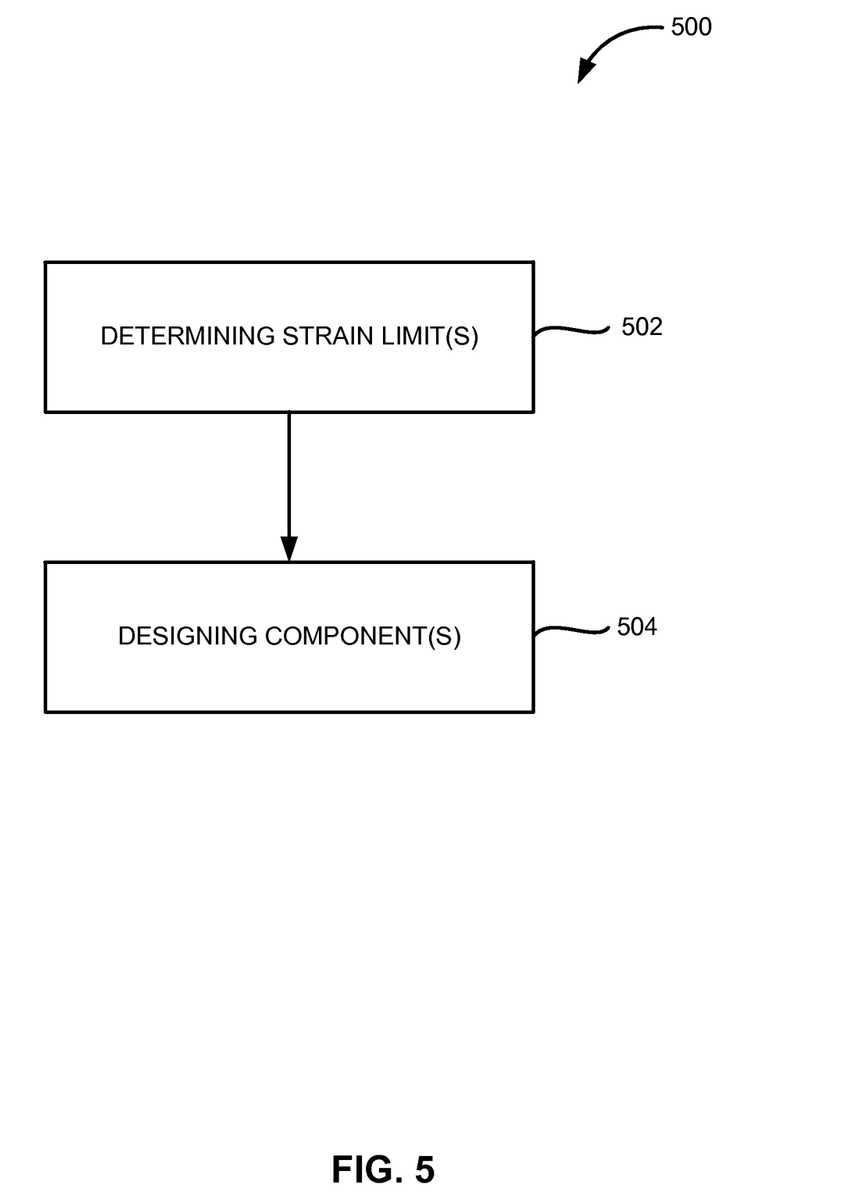
FIG. 5 illustrates a method for designing devices, according to various embodiments.

A method 500 of designing devices based on determining the strain limit(s) of materials before cracking is illustrated in FIG. 5. According to various embodiments, method 500 comprises determining the strain limit(s) 502 of at least one material; and designing component 504 based on the determined strain limit.

According to various embodiments, determining the strain limit(s) 502 may include determining the strain limits of multiple materials and selecting at least one advantageous material for designing the device in designing component 504 based on the determined strain limit(s). In determining the advantageous material, additional factors may be considered in conjunction with the determined strain limit, such as cost, availability, etc. The term "material" in determining the strain limit(s) 502 may refer to the coating material, including a single coating and multiple layered coating, and the combined coating(s) and substrate material. Additionally, the term "material" may take into account at least one variable property associated with the material, which may affect the material's strain limit. Such variable property may include, for example, the application conditions for applying a coating, for example by HVOF techniques, such as, for example, fuel, oxygen, application velocity, condition of the application apparatus, thickness of coating, etc. Thus, determining the advantageous material may include determining an advantageous variable property which will make the material most crack resistant, such as coating thickness for specific coating(s), application parameters for the specific coating(s), conditions for coating equipment (e.g. condition of equipment, application speed, heat, etc.), coating/substrate combination, combination of coatings for multicoated substrates, etc.

According to various embodiments, determining the strain limit(s) 502 may be performed using test method 100 including using a 4-point bend test, as described above.

According to various embodiments, step 504 of designing the at least one component comprises designing the component to be crack resistant based on the known strain limit of the coated material to be used, in conjunction with the known operational conditions for the component. For example, the wall thickness of the component may be increased to resist bending beyond the bending limit of the coated material. Conversely, the wall thickness of the component may be decreased, to design a lighter component of minimal thickness, if the bending limit of the coated material allows for such adjustment.

Additionally, operational conditions may be adjusted to operate below the determined cracking limit.

Accordingly, benefits of the above method may include eliminating the risk of cracking of coated devices, reducing weight of coating and/or coated devices (by designing according to minimal thickness).

Systems and methods are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for determining the strain limits of a material, comprising:
   loading a test specimen comprising the material, in a load fixture, wherein the load fixture comprises a single top retaining block and a bottom retaining block configured to retain the test specimen therebetween, the retaining blocks comprising a first contact member configured to contact the test specimen at a first contact point, a second contact member configured to contact the test specimen at a second contact point, a third contact member configured to contact the test specimen at a third contact point, and a fourth contact member configured to contact the test specimen at a fourth contact point, the top retaining block further comprising an observation hole, which extends through the top retaining block, and is aligned with the test specimen;
   applying a mechanical load to the test specimen through the first contact member at the first contact point, through the second contact member at the second contact point, through the third contact member at the third contact point, and through the fourth contact member at the fourth contact point, wherein the first contact member, the second contact member, the third contact member, and the fourth contact member are together configured to impart a bending load onto the test specimen; and
   observing the test specimen through the observation hole for detection of cracking while the mechanical load is applied.

2. The method of claim 1 wherein applying the mechanical load comprises applying gradually increasing pressure.

3. The method of claim 1, further comprising observing the test specimen under magnification.

4. The method of claim 1, wherein the material comprises at least one of a coating, and a coated material.

5. The method of claim 1 wherein the test specimen comprises a substrate having a top surface and a coating covering a portion of the top surface, and leaving an uncoated portion of the top surface.

6. The method of claim 5 wherein the first contact point, the second contact point, the third contact point, and the fourth contact point are uncoated.

7. A test system for determining the effects of strain on a material comprising:
   a load fixture configured to retain a test specimen,
   the load fixture comprising a single top retaining block and a bottom retaining block for retaining the test specimen therebetween,
   the top retaining block comprising a top load contact member configured to contact the test specimen at a top contact point on the test specimen, and
   the bottom retaining block comprising a bottom load contact member configured to contact the test specimen at a bottom contact point on the test specimen, and
   the top retaining block comprising an observation hole, which extends entirely through the top retaining block perpendicular to the test specimen, such that a portion of the test specimen is visible through the observation hole,
   wherein the top load contact member further comprises a first pair of contact saddles, having a first distance therebetween, and configured to contact the test specimen at a top surface of the test specimen in response to the test specimen being retained, and
   wherein the bottom load contact member further comprises a second pair of contact saddles, having a second distance therebetween, and configured to contact the test specimen at a bottom surface of the test specimen in response to the test specimen being in retention,
   wherein the first distance is different from the second distance.

8. The system of claim 7, wherein the test specimen comprises a substrate, and wherein the top surface of the test specimen comprises a coated portion and an uncoated portion.

9. The system of claim 8 wherein the first pair of contact saddles are configured to contact the test specimen at the uncoated portion.

10. The system of claim 8, the test specimen comprising a beveled top edge extending from the top surface.

11. The system of claim 7, the top load contact member comprising a top pair of contact saddles configured to contact the test specimen at a top surface of the test specimen at centrally equidistant points with respect to one another, and
   the bottom load contact member comprising a bottom pair of contact saddles configured to contact the test specimen at a bottom surface of the test specimen at centrally equidistant points with respect to one another.

12. A method for designing a device, comprising:
   determining a strain limit of a material, the material comprising a coating, the strain limit being the strain value which the material can accommodate before the coating cracks, wherein the strain limit is determined by
      applying a mechanical load through a first contact member at a first contact point with the material, through a second contact member at a second contact point with the material, through a third contact member at a third contact point with the material, and through a fourth contact member at a fourth contact point with the material, wherein the first contact member, the second contact member, the third contact member, and the fourth contact member are together configured to impart a bending load onto the material, and observing the material for cracking as the mechanical load is being applied; and designing at least one portion of the device based upon the determined strain limit, the device comprising the material.

13. The method of claim 12, further comprising:

determining strain limits of a plurality of materials;

selecting at least one advantageous material based on the determined stain limits; and using the advantageous material in the designing.

14. The method of claim 12, the material comprising at least one variable property affecting the material's strain limit, wherein the determined strain limit is associated with the material's variable property.

15. The method of claim 14, further comprising:

determining multiple strain limits associated with a plurality of variable properties of the material;

selecting at least one advantageous variable property for the material based on the determined stain limits; and using the advantageous variable property in the designing.

16. The method of claim 12 wherein the designing is further based on intended operational conditions for the device.

17. The method of claim 16, further comprising designing the device to resist cracking under the intended operational conditions.

18. The method of claim 12, further comprising:

determining strain limits of a plurality of materials, each of the plurality of materials comprising at least one variable property affecting the material's strain limit, wherein the determined strain limits is associated with the material's variable property;

selecting at least one advantageous material based on the determined stain limits; and using the advantageous material in the designing.

\* \* \* \* \*